(12) United States Patent
Despotopulos et al.

(10) Patent No.: US 11,587,694 B2
(45) Date of Patent: Feb. 21, 2023

(54) METHODS OF ISOLATING RADIOACTIVE MERCURY AND USES THEREOF

(71) Applicant: LAWRENCE LIVERMORE NATIONAL SECURITY, LLC, Livermore, CA (US)

(72) Inventors: John Despotopulos, Livermore, CA (US); Carlos Valdez, San Ramon, CA (US); Kelly Nora Kmak, Berkeley, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 345 days.

(21) Appl. No.: 16/816,822

(22) Filed: Mar. 12, 2020

(65) Prior Publication Data

US 2021/0287822 A1    Sep. 16, 2021

(51) Int. Cl.
*G21G 1/00* (2006.01)
*G21G 4/08* (2006.01)
*A61N 5/10* (2006.01)

(52) U.S. Cl.
CPC .......... *G21G 1/001* (2013.01); *A61N 5/1001* (2013.01); *G21G 4/08* (2013.01); *A61N 2005/1019* (2013.01); *G21G 2001/0094* (2013.01)

(58) Field of Classification Search
CPC .... A61N 5/10–1084; A61N 2005/1085–1098; G21G 1/001; G21G 1/10; G21G 2001/0094; G21G 4/08
See application file for complete search history.

(56) References Cited

U.S. PATENT DOCUMENTS 6,696,576 B2 *  2/2004  Baumann .................. C02F 1/64
                                                      252/390

OTHER PUBLICATIONS

Chodil et al. (1967) (p,n) and (p,2n) cross sections on nine elements between 7.0 and 15.0 MeV. Nucl Phys A 93:648-672.
Despotopulos et al., (2018), Production and isolation of $^{197m,g}$Hg. J. Radioanal. Nucl. Chem., 317:985-989.
Despotopulos JD, et al. (2015) Production and isolation of carrier-free homologs of flerovium and element 115 at the Lawrence Livermore National Laboratory Center for Accelerator Mass Spectrometry. J Radioanal Nucl Chem 308:567-572.
Ghosh et al. (2016) Separation of no-carrer-added 197m,gHg, 197mHg from Au target ionic liquid and salt based aqueous biphasic systems. J Radioanal Nucl Chem 310:1381-1396.
Greif et al., Distribution of radiomercury administered as labelled chlormerodrin (Neohydrin) in the kidneys for rats and dogs, J. Clin. Investig., 35:38-43 (1956).
Hara et al. (1973) Cyclotron production of 197mHg and its use for lung tumor imaging. Int J Appl Radiat Isot 24:66.
Mandal et al. (2010) Production, separation and speciation of no-carrier-added Hg radionuclides using greener methodologies. Radiochim Acta 98:45-51.
Mantricali (1969) Brain scanning by means of 197Hg-labelled neohydrin. Psychiatr Neurol Neurochir 72:89-95.
National Nuclear Data Center "NNDC" (2013) Brookhaven National Laboratory. http://www.nndc.bnl.gov/.
Pederson (1988) Macrocyclic polyethers: dibenzo-18-crown-6 polyether and dicyclohexyl-18-crown-6 polyether. Org Synth 9:395-400.
Sudar et al., Cross sections for the formation of $^{195}$Hg$^{m,g}$, $^{197}$Hg$^{m,g}$, and $^{196}$Au$^{m,g}$ in alpha and $^3$He-particle induced reactions on Pt: Effect of level density parameters on the calculated isomeric cross-section ratio, Phys. Rev. C, 73:034613 (2006).
Walther et al., Theranostic mercury part 1: a new Hg/Au separation by a resin based method, AIP Conf. Proc., 1845:020023 (2017).
Walther et al., Theranostic mercury: 197(m)Hg with high specific activity for imaging and therapy, App. Radiat. Isot., 97:177-181 (2015).
Wilkniss et al. (1972) Production of carrier-free 197m, 197Hg with a cyclotron. Radiochim Acta 17:110-113.

* cited by examiner

*Primary Examiner* — Thaddeus B Cox
(74) *Attorney, Agent, or Firm* — Marshall, Gerstein & Borun LLP

(57) ABSTRACT

Provided herein are methods of isolating and using radioactive mercury. In particular, provided herein are methods of isolating radioactive mercury including the use of a thia-crown ether, and using the isolated radioactive mercury in therapeutic and/or imaging applications.

21 Claims, No Drawings

METHODS OF ISOLATING RADIOACTIVE MERCURY AND USES THEREOF

STATEMENT REGARDING FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

Radioactive mercury can be useful in both therapeutic and imaging applications. In the 1950s and 1960s, mercury isotopes with low specific activities—prepared from neutron reactions on natural mercury—were used for imaging, but the high toxicity and long biological half-life associated with mercury led to its demise as a radiopharmaceutical. The recent production of radiopharmaceuticals by charged particle reactions allows for no-carrier-added (NCA) radionuclides to be produced. This has led to a renewed interested in radioactive mercury, such as $^{197m}$Hg and $^{197g}$Hg, for imaging and therapy since they can be produced in large quantities without the toxic stable mercury present. The dominant reactions for producing these radionuclides includes irradiating platinum with alpha particles, or gold with protons, which can result in little to no stable mercury.

However, these methods have significant drawbacks, such as product loss, low efficiency, and difficult and timely post-processing of purified material. Thus, improved methods for preparing and isolating radioactive mercury are needed.

SUMMARY

Provided herein are methods of isolating radioactive mercury comprising extracting the radioactive mercury from an aqueous solution with an organic solution comprising thiacrown ether to form an extracted solution, and isolating the radioactive mercury from the extracted solution.

In various embodiments, the radioactive mercury comprises $^{197m}$Hg, $^{197g}$Hg, or a combination thereof. In various embodiments, the radioactive mercury is no-carrier-added $^{197m,g}$Hg.

In various embodiments, the thiacrown ether comprises dibenzohexathia-18-crown-6 ether, 1,4,7,10,13,16-hexathiacyclooctadecane, (2Z,5Z,8Z,11Z,14Z,17Z)-1,4,7,10,13,16-hexathiacyclooctadeca-2,5,8,11,14,17-hexaene, or a combination thereof. In some cases, the thiacrown ether comprises dibenzohexathia-18-crown-6 ether.

In various embodiments, the aqueous solution has an acid concentration of less than 1 M. In some cases, the aqueous solution comprises nitric acid, hydrochloric acid, or a combination thereof.

In various embodiments, the isolating comprises admixing the extracted solution and a strong acid to extract the radioactive mercury from the extracted solution, wherein the strong acid is selected from the group consisting of hydrochloric acid, nitric acid, hydrobromic acid, hydroiodic acid, and any combination thereof. In some cases, the strong acid has a concentration of at least 1.5 M. In some cases, the strong acid has a concentration of at least 6 M.

In various embodiments, the radioactive mercury is prepared by irradiating platinum foil with alpha particles to form the radioactive mercury. In some cases, the alpha particles have a kinetic energy of 20 MeV to 25 MeV.

In various embodiments, the radioactive mercury is prepared by irradiating gold foil with protons to form the radioactive mercury. In some cases, the protons have a kinetic energy of 10 MeV to 15 MeV.

In various embodiments, the method is carried out in one hour or less.

Further provided is the radioactive mercury prepared by the process of any one of methods described herein.

Also provided are methods comprising administering the radioactive mercury of the disclosure to a subject.

In various embodiments, the radioactive mercury comprises $^{197m}$Hg and the method further comprises subjecting the subject to an imaging modality. In some cases, the imaging modality is selected from the group consisting of positron emission tomography (PET), positron emission tomography/computed tomography (PET/CT), positron emission tomography/magnetic resonance imaging (PET/MRI), single-photon emission computerized tomography (SPECT), and single-photon emission computerized tomography/computed tomography (SPECT/CT).

In various embodiments, the radioactive mercury comprises $^{197g}$Hg and the radioactive mercury is administered in a therapeutically effective amount.

In various embodiments, the subject is human. In various embodiments, the subject suffers from cancer.

Also provided are pharmaceutical compositions comprising the radioactive mercury of the disclosure and a pharmaceutically acceptable carrier, wherein the radioactive mercury comprises $^{197g}$Hg.

Further aspects and advantages will be apparent to those of ordinary skill in the art from a review of the following detailed description. The description hereafter includes specific embodiments with the understanding that the disclosure is illustrative, and is not intended to limit the invention to the specific embodiments described herein.

DETAILED DESCRIPTION

Provided herein are methods of isolating and using radioactive mercury. In particular, the methods of the disclosure include use of a thiacrown ether.

Methods of Isolating Radioactive Mercury

The disclosure provides methods of isolating radioactive mercury. In embodiments, the radioactive mercury includes $^{197m}$Hg, $^{197g}$Hg, or a combination thereof. As would be understood by the person of ordinary skill in the art, a radionuclide labeled with "m" means that the radionuclide is in an excited—or metastable—state, whereas a radionuclide labeled with "g" means that the radionuclide is in the stable, ground state. As used herein, the term "$^{197m,g}$Hg" refers to a mixture of each of $^{197m}$Hg and $^{197g}$Hg. In embodiments, the radioactive mercury is no-carrier-added $^{197m,g}$Hg. No-carrier-added (NCA) radioactive mercury is radioactive mercury in which no carrier atoms have been added and for which precautions have been taken to minimize contamination with stable isotopes of mercury. Advantageously, NCA radioactive mercury can be used in therapeutic and imaging applications, as there is no significant risk of toxicity, due to the radioactive mercury being free of stable mercury. In embodiments, the methods disclosed herein provide NCA radioactive mercury.

Radioactive mercury used in the methods disclosed herein can be prepared according to methods that are known in the art. In embodiments, the radioactive mercury is prepared by irradiating platinum foil with alpha particles to form the radioactive mercury. The alpha particles can have a kinetic energy of at least 20, 21, 22, or 23 MeV and/or up to 25, 24, 23, or 22 MeV. In embodiments, the alpha particles have a kinetic energy of 20 MeV to 25 MeV. In embodiments, the radioactive mercury is prepared by irradiating gold foil with protons to form the radioactive mercury. The protons can have a kinetic energy of at least 10, 11, 12, or 13 MeV and/or up to 15, 14, 13, or 12 MeV. In embodiments, the protons having a kinetic energy of 10 MeV to 15 MeV.

The methods of the disclosure include extracting the radioactive mercury from an aqueous solution with an organic solution comprising a thiacrown ether to form an extracted solution. The radioactive mercury can be extracted from the aqueous solution, for example, by admixing the aqueous solution with the organic solution to provide an admixture having an organic phase and aqueous phase. In general, admixing the solutions allows the thiacrown ether (in the organic solution) and radioactive mercury (in the aqueous solution) to interact and form a thiacrown ether-radioactive mercury complex in the organic phase. The organic phase can then be separated from the aqueous phase via extraction to provide the extracted solution.

In accordance with embodiments, the aqueous solution includes the radioactive mercury. For example, in embodiments wherein a platinum or gold foil is irradiated with alpha particles or protons, respectively, the irradiated foil—containing the radioactive mercury—can be dissolved in an aqueous solution. In embodiments, the aqueous solution has an acid concentration of less than 1 M, for example, 0.9 M, 0.8 M, 0.7 M, 0.6 M, 0.5 M, 0.4 M, 0.3 M, 0.2 M, 0.1 M, 0.05 M, 0.01 M, 0.001 M, or 0.0001 M. In embodiments, the aqueous solution includes nitric acid, hydrochloric acid, or a combination thereof. In embodiments, the aqueous solution includes nitric acid. In embodiments, the aqueous solution includes hydrochloric acid. In embodiments, the aqueous solution includes a diluted aqua regia solution. As would be understood and appreciated by the person of ordinary skill in the art, aqua regia is a concentrated 1:3 $HNO_3$:HCl solution.

In accordance with embodiments, the organic solution includes the thiacrown ether. In embodiments, the thiacrown ether includes dibenzohexathia-18-crown-6-ether, 1,4,7,10, 13,16-hexathiacyclooctadecane, (2Z,5Z,8Z,11Z,14Z,17Z)-1,4,7,10,13,16-hexathiacyclooctadeca-2,5,8,11,14,17-hexaene, or a combination thereof. In embodiments, the thiacrown ether includes dibenzohexathia-18-crown-6-ether. In embodiments, the thiacrown ether includes 1,4,7, 10,13,16-hexathiacyclooctadecane. The 1,4,7,10,13,16-hexathiacyclooctadecane can be prepared as described in Wolf, R. E. et al. "Crown thioether chemistry: structural and conformational studies of tetrathia-12-crown-4, pentathia-15-crown-5, and hexathia-18-crown-6. Implications for ligand design" J. Am. Chem. Soc. 1987, 109, 4328-4335. In embodiments, the thiacrown ether includes (2Z,5Z,8Z,11Z, 14Z,17Z)-1,4,7,10,13,16-hexathiacyclooctadeca-2,5,8,11, 14,17-hexaene. The (2Z,5Z,8Z,11Z,14Z,17Z)-1,4,7,10,13, 16-hexathiacyclooctadeca-2,5,8,11,14,17-hexaene can be prepared as described in Tsuchiya, T.; Shimizu, T.; Kamigata, N. "Unsaturated Thiacrown Ethers: Synthesis, Physical Properties, and Formation of a Silver Complex" J. Am. Chem. Soc. 2001, 123, 11534-11538. Prior to the present disclosure, thiacrown ethers were not believed to be useful in the isolation of radioactive mercury prepared according to the disclosure, as these thiacrown ethers were also known to effectively bind to the remaining platinum and gold atoms in the irradiated foil. However, the thiacrown ethers of the disclosure can selectively bind radioactive mercury in the presence of platinum or gold. In embodiments, the thiacrown ether can be present in the organic solution at a concentration of $10^{-5}$ to $10^{-3}$ M. The thiacrown ether can be dissolved in any suitable organic solvent, for example, carbon tetrachloride, benzene, nitrobenzene, dimethylsulfide, or a combination thereof. In embodiments, the thiacrown ether is dissolved in a carbon tetrachloride solution.

In accordance with embodiments, the aqueous solution and organic solution can be mixed, such that the radioactive mercury can be extracted from the aqueous solution with the organic solution to form an extracted solution. Thus, in accordance with embodiments, the extracted solution can include the thiacrown ether and the radioactive mercury. The aqueous solution and the organic solution can be mixed for a period of time ranging from 5 minutes to 30 minutes, for example at least about 5, 10, 15, or 20 minutes and/or up to 30, 25, 20, or 15 minutes.

The methods of disclosure further provide isolating the radioactive mercury from the extracted solution.

In embodiments, isolating the radioactive mercury includes admixing the extracted solution with a strong acid. The strong acid can include hydrochloric acid, nitric acid, hydrobromic acid, hydroiodic acid, or any combination thereof. In embodiments, the strong acid includes hydrochloric acid. The strong acid can have a concentration of at least 1.5, 2, 3, 4, 5, 6, 7, 8, or 10 M and/or up to 10, 8, 7, 6, or 5 M. In embodiments, the strong acid has a concentration of at least 1.5 M. In embodiments, the strong acid has a concentration of at least 6 M.

In embodiments, the methods disclosed herein can be performed in about 2 hours or less, for example, 1.5 hours or less, 1 hour or less, or 45 minutes or less. In embodiments, the methods can be performed in one hour or less. The duration of the disclosed methods—from the dissolution of foil, to the isolation of the radioactive mercury—can be shortened, for example, by reducing admixing times or by using a centrifuge to reduce the time needed to allow the phases to settle after admixing.

Radioactive Mercury and Methods of Use

The disclosure further provides radioactive mercury isolated according to the methods described herein, as well as methods of using the same.

In embodiments, the radioactive mercury can be administered to a subject. In embodiments, the subject is a mammal. In embodiments, the subject is human. In embodiments, the subject suffers from or is suspected to suffer from cancer. The manner of administration of the radioactive mercury is not particularly limited. For example, in embodiments, the radioactive mercury can be administered intravenously. The manner of administration and dose thereof would be within the purview of the doctor, nurse, or radiologist trained to administer the radioactive mercury.

In embodiments, the administered radioactive mercury includes $^{197m}Hg$, and the method further includes subjecting the subject to an imaging modality. The imaging modality can be selected from positron emission tomography (PET), positron emission tomography/computed tomography (PET/CT), positron emission tomography/magnetic resonance imaging (PET/MRI), single-photon emission computerized tomography (SPECT), and single-photon emission computerized tomography/computed tomography (SPECT/CT). Due to the half-life of $^{197m}Hg$ (23.8 hours), in embodiments, the subject is subjected to the imaging modality within 0.5 hours to 7 days after administration, for example 1 hour to 12 hours, 5 hours to 5 days, 12 hours to 3 days, or 1 day to 2 days. In some cases, the subject is subjected to the imaging modality at 0.5 hours, 1 hour, 2 hours, 5 hours, 6 hours, 8 hours, 12 hours, 18 hours, 1 day, 2 days, 3 days, 4 days, 5 days or 7 days after administration of the radioactive mercury.

In embodiments, the administered radioactive mercury includes $^{197g}$Hg, and the radioactive mercury is administered to a subject in a therapeutically effective amount. As used herein, the term "therapeutically effective amount" means an amount of the radioactive mercury effective to achieve the desired therapeutic response for a particular subject, composition, and mode of administration, without being toxic to the subject. As would be understood by the person of ordinary skill in the art, the therapeutically effective amount will depend on several factors including the overall health of a subject, and the formulation and route of administration of the radioactive mercury. In embodiments, the subject suffers from cancer and the therapeutically effective amount is to achieve a therapeutic response against that cancer.

The disclosure further provides a pharmaceutical composition comprising the radioactive mercury of the disclosure and a pharmaceutically acceptable carrier. In embodiments, the radioactive mercury in the pharmaceutical composition includes $^{197g}$Hg. As used herein, the term "carrier" means any pharmaceutically acceptable additive, excipient, diluent, adjuvant, or other ingredient, other than the active pharmaceutical ingredient (API). The term "pharmaceutically acceptable carrier" refers to a medium that does not interfere with the effectiveness of the biological activity of the active ingredient(s) and is not toxic to the host to which it is administered.

EMBODIMENTS

Specifically contemplated embodiments of the disclosure are herein described in the following numbered paragraphs. These embodiments are intended to be illustrative in nature and not intended to be limiting.

Embodiment 1. A method of isolating radioactive mercury comprising:

extracting the radioactive mercury from an aqueous solution with an organic solution comprising thiacrown ether to form an extracted solution; and, isolating the radioactive mercury from the extracted solution.

Embodiment 2. The method of embodiment 1, wherein the radioactive mercury comprises $^{197m}$Hg, $^{197g}$Hg, or a combination thereof.

Embodiment 3. The method of embodiment 1 or 2, wherein the thiacrown ether comprises dibenzohexathia-18-crown-6 ether, 1,4,7,10,13,16-hexathiacyclooctadecane, (2Z,5Z,8Z,11Z,14Z,17Z)-1,4,7,10,13,16-hexathiacyclooctadeca-2,5,8,11,14,17-hexaene, or a combination thereof.

Embodiment 4. The method of embodiment 2, wherein the thiacrown ether comprises dibenzohexathia-18-crown-6 ether.

Embodiment 5. The method of any one of embodiments 1 to 4, wherein the aqueous solution has an acid concentration of less than 1 M.

Embodiment 6. The method of embodiment 5, wherein the aqueous solution comprises nitric acid, hydrochloric acid, or a combination thereof.

Embodiment 7. The method of any one of embodiments 1 to 6, wherein the isolating comprises admixing the extracted solution and a strong acid to extract the radioactive mercury from the extracted solution, wherein the strong acid is selected from the group consisting of hydrochloric acid, nitric acid, hydrobromic acid, hydroiodic acid, and any combination thereof.

Embodiment 8. The method of embodiment 7, wherein the strong acid has a concentration of at least 1.5 M.

Embodiment 9. The method of embodiment 7 or 8, wherein the strong acid has a concentration of at least 6 M.

Embodiment 10. The method of any one of embodiments 1 to 9, wherein the radioactive mercury is prepared by irradiating platinum foil with alpha particles to form the radioactive mercury.

Embodiment 11. The method of embodiment 10, wherein the alpha particles have a kinetic energy of 20 MeV to 25 MeV.

Embodiment 12. The method of any one of embodiments 1 to 9, wherein the radioactive mercury is prepared by irradiating gold foil with protons to form the radioactive mercury.

Embodiment 13. The method of embodiment 12, wherein the protons have a kinetic energy of 10 MeV to 15 MeV.

Embodiment 14. The method of any one of embodiments 1 to 13, wherein the method is carried out in one hour or less.

Embodiment 15. The method of any one of embodiments 1 to 14, wherein the radioactive mercury is no-carrier-added $^{197m,g}$Hg.

Embodiment 16. The radioactive mercury prepared by the process of any one of embodiments 1 to 15.

Embodiment 17. A method comprising administering the radioactive mercury of embodiment 16 to a subject.

Embodiment 18. The method of embodiment 17, wherein the radioactive mercury comprises $^{197m}$Hg and the method further comprises subjecting the subject to an imaging modality.

Embodiment 19. The method of embodiment 18, wherein the imaging modality is selected from the group consisting of positron emission tomography (PET), positron emission tomography/computed tomography (PET/CT), positron emission tomography/magnetic resonance imaging (PET/MRI), single-photon emission computerized tomography (SPECT), and single-photon emission computerized tomography/computed tomography (SPECT/CT).

Embodiment 20. The method of embodiment 17, wherein the radioactive mercury comprises $^{197g}$Hg and the radioactive mercury is administered in a therapeutically effective amount.

Embodiment 21. The method of any one of embodiments 17 to 20, wherein the subject is human.

Embodiment 22. The method of any one of embodiments 17 to 21, wherein the subject suffers from cancer.

Embodiment 23. A pharmaceutical composition comprising the radioactive mercury of embodiment 16 and a pharmaceutically acceptable carrier, wherein the radioactive mercury comprises $^{197g}$Hg.

EXAMPLES

Example 1—Synthesis of Dibenzohexathia-18-Crown-6 Ether

Dibenzohexathia-18-crown-6 ether was prepared according to the following reaction scheme:

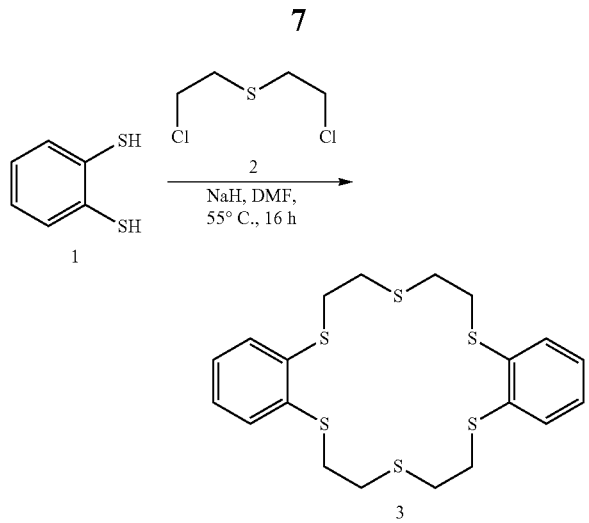

Double treatment of 1,2-benzenedithiol 1 with one equivalent of NaH in the presence of bis-(2-chloroethyl) sulfide ether 2 provided dibenzohexathia-18-crown-6 ether 3.

1,2-benzenedithiol (1, 0.84 g, 5.9 mmol) was taken up in dimethylformamide (20 mL) in a 100 mL round bottomed flask equipped with a stir bar and treated with sodium hydride (NaH, 170 mg, 7.1 mmol, 1.2 equiv. to dithiol). The resulting suspension was treated with bis-(2-chloroethyl) sulfide (0.38 g, 2.4 mmol) and stirred for 4 hours at 55° C. After 4 hours, a second treatment of the mixture with sodium hydride (170 mg) was done and then the resulting mixture was treated with another aliquot of bis-(2-chloroethyl)sulfide (0.38 g). The resulting final mixture was then stirred at 55° C. overnight. After the overnight stirring, the mixture was quenched with MeOH (5 mL) and transferred to a separatory funnel where it was partitioned ($CH_2Cl_2/H_2O$). The organic phase was washed with water (2×10 mL), dried over anhydrous $Na_2SO_4$ and evaporated in vacuo and purified by flash column chromatography (hexanes→5% EtOAc:hexanes) to furnish dibenzothiacrown ether 3. $R_f$ (1:9 EtOAc:hexanes): 0.78; $^1H$ NMR (600 MHz, $CDCl_3$) δ 7.31 (m, 4H), 7.25 (m, 4H), 3.09 (m, 8H), 2.90 (m, 8H); $^{13}C$ NMR (151 MHz, $CDCl_3$) δ 134.6, 130.1, 124.4, 35.6, 34.0.

Example 2—Preparation and Isolation of $^{197m,g}Hg$

A 30-60 mg high purity $^{nat}Pt$ and $^{nat}Au$ foil (99.99+%) was obtained from Goodfellow. The foil was cut into 8×8-mm squares weighing 20-50 mg each and mounted in a target chamber. The foil was irradiated with 20-25 MeV alpha particles for 3-8 hours at currents of 100-600 nA using the tandem Van-de-Graaff accelerator at the Center for Accelerator Mass Spectrometry (CAMS). The foils were immediately removed from the target chamber for dissolution.

Following irradiation, the foil was dissolved in 3 mL aqua regia (1:3 $HNO_3$:HCl) and gently heated. A 75 μL sample of the resulting solution (containing approximately 1.4 mg of irradiated Pt or Au) was diluted to 2.5 mL with 0.001 M $HNO_3$ to provide the aqueous solution. To this solution, a 2.5 mL carbon tetrachloride solution containing $10^{-4}$ M of dibenzohexathia-18-crown-6 ether was added. The phases were mixed in a 5 mL centrifuge tube for 30 minutes and allowed to settle for 10 minutes. A 1.5 μL aliquot of each phase was taken and counted by HPGe gamma spectroscopy. Organic phase: $^{197m}Hg$ ($E_\gamma$=133.99 keV, $t_{1/2}$=23.8 hours); Aqueous phase: Pt (traced with $^{191}Pt$) ($E_\gamma$=538.9 keV, $t_{1/2}$=2.80 days), Au (traced with $^{198}Au$ produced from neutron reactions within the gold target) ($E_\gamma$=411.8 keV, $t_{1/2}$=2.69 days). No detectable amount of the Pt or Au foil was seen in the organic phase.

The organic phase, including $^{197m,g}Hg$, was then back extracted with 1.5 mL of 8 M HCl for 30 minutes, followed by 10 minutes to allow settling. A 1 μL aliquot of each phase was taken for HPGe gamma spectroscopy. Back extraction was performed in triplicate.

Recoveries are shown in Table 1, below.

TABLE 1

Summary of $^{197m,g}Hg$ separation of Example 2

| Foil | Extraction | Matrix | $^{197m,g}Hg$ Recovered (%) |
|---|---|---|---|
| Pt | First extraction | 1.4 mg Pt in 75 μL aqua regia diluted to 2.5 mL with 0.001M $HNO_3$ | 98.9 ± 0.4 |
| Pt | Back extraction | 8M HCl | 99.8 ± 0.7 |
| Au | First extraction | 1.5 mg Au in 75 μL aqua regia diluted to 2.5 mL with 0.001M $HNO_3$ | 90 ± 10 |
| Au | Back Extraction | 8M HCl | 99 ± 10 |

As can be seen from Table 1, the first extraction of $^{197m,g}Hg$ was extremely high and the following back extraction of the $^{197m,g}Hg$ into the aqueous phase was nearly 100%, within error.

Accordingly, Example 2 demonstrates that the method according to the disclosure is an extremely fast method to selectively isolate radioactive mercury using a thiacrown ether.

What is claimed is:

1. A method of isolating radioactive mercury comprising:
   extracting the radioactive mercury from an aqueous solution with an organic solution comprising thiacrown ether to form an extracted solution; and,
   isolating the radioactive mercury from the extracted solution.

2. The method of claim 1, wherein the radioactive mercury comprises $^{197m}Hg$, $^{197g}Hg$, or a combination thereof.

3. The method of claim 1, wherein the thiacrown ether comprises dibenzohexathia-18-crown-6 ether, 1,4,7,10,13,16-hexathiacyclooctadecane, (2Z,5Z,8Z,11Z,14Z,17Z)-1,4,7,10,13,16-hexathiacyclooctadeca-2,5,8,11,14,17-hexaene, or a combination thereof.

4. The method of claim 3, wherein the thiacrown ether comprises dibenzohexathia-18-crown-6 ether.

5. The method of claim 1, wherein the aqueous solution has an acid concentration of less than 1 M.

6. The method of claim 5, wherein the aqueous solution comprises nitric acid, hydrochloric acid, or a combination thereof.

7. The method of claim 1, wherein the isolating comprises admixing the extracted solution and a strong acid to extract the radioactive mercury from the extracted solution, wherein the strong acid is selected from the group consisting of hydrochloric acid, nitric acid, hydrobromic acid, hydroiodic acid, and any combination thereof.

8. The method of claim 7, wherein the strong acid has a concentration of at least 1.5 M.

9. The method of claim 7, wherein the strong acid has a concentration of at least 6 M.

10. The method of claim 1, wherein the radioactive mercury is prepared by irradiating platinum foil with alpha particles to form the radioactive mercury.

11. The method of claim 10, wherein the alpha particles have a kinetic energy of 20 MeV to 25 MeV.

12. The method of claim 1, wherein the radioactive mercury is prepared by irradiating gold foil with protons to form the radioactive mercury.

13. The method of claim 12, wherein the protons have a kinetic energy of 10 MeV to 15 MeV.

14. The method of claim 1, wherein the method is carried out in one hour or less.

15. The method of claim 1, wherein the radioactive mercury is no-carrier-added $^{197m,g}$Hg.

16. A pharmaceutical composition comprising the radioactive mercury isolated according to the process of claim 1 and a pharmaceutically acceptable carrier, wherein the radioactive mercury comprises $^{197g}$Hg.

17. A method comprising
    extracting radioactive mercury from an aqueous solution with an organic solution comprising thiacrown ether to form an extracted solution;
    isolating the radioactive mercury from the extracted solution; and,
    administering the radioactive mercury to a subject.

18. The method of claim 17, wherein the radioactive mercury comprises $^{197m}$Hg and the method further comprises subjecting the subject to an imaging modality.

19. The method of claim 18, wherein the imaging modality is selected from the group consisting of positron emission tomography (PET), positron emission tomography/computed tomography (PET/CT), positron emission tomography/magnetic resonance imaging (PET/MRI), single-photon emission computerized tomography (SPECT), and single-photon emission computerized tomography/computed tomography (SPECT/CT).

20. The method of claim 17, wherein the radioactive mercury comprises $^{197g}$Hg and the radioactive mercury is administered in a therapeutically effective amount.

21. The method of claim 17, wherein the subject suffers from cancer.

* * * * *